United States Patent
Hayashi et al.

(10) Patent No.: US 8,030,093 B2
(45) Date of Patent: Oct. 4, 2011

(54) DISPENSING MECHANISM, DISPENSING APPARATUS AND DISPENSING METHOD FOR LIQUID TO BE DISPENSED

(75) Inventors: Masayoshi Hayashi, Amagasaki (JP); Kazuhito Tanimoto, Amagasaki (JP); Keiko Sasaki, Amagasaki (JP)

(73) Assignee: Wako Pure Chemical Industries, Ltd., Osaka-shi (JP)

( * ) Notice: Subject to any disclaimer, the term of this patent is extended or adjusted under 35 U.S.C. 154(b) by 215 days.

(21) Appl. No.: 12/298,072

(22) PCT Filed: Apr. 24, 2006

(86) PCT No.: PCT/JP2006/308562
§ 371 (c)(1), (2), (4) Date: Dec. 12, 2008

(87) PCT Pub. No.: WO2007/122732
PCT Pub. Date: Nov. 1, 2007

(65) Prior Publication Data
US 2009/0098024 A1 Apr. 16, 2009

(51) Int. Cl.
 G01N 33/543 (2006.01)
 B01L 3/00 (2006.01)
 B01L 3/02 (2006.01)
(52) U.S. Cl. .............. 436/518; 422/501; 73/864.01
(58) Field of Classification Search .......... 436/518; 422/501; 73/864.01
See application file for complete search history.

(56) References Cited

U.S. PATENT DOCUMENTS 5,312,757 A * 5/1994 Matsuyama et al. ......... 436/54
5,854,082 A 12/1998 Kubotsu et al. ............. 436/518
6,015,679 A 1/2000 Kubotsu et al. ............. 435/7.1
6,734,424 B2 * 5/2004 Lennon et al. .............. 250/288
2004/0048397 A1 * 3/2004 Yokoi ......................... 436/518

FOREIGN PATENT DOCUMENTS

| JP | 57-42856 | 3/1982 |
| JP | 62-228952 | 10/1987 |
| JP | 4-329363 | 11/1992 |
| JP | 7-110331 | 4/1995 |
| JP | 7-140147 | 6/1995 |
| JP | 2003-149093 A1 | 5/2003 |

OTHER PUBLICATIONS

International Search Report for International Application No. PCT/JP2006/308562 dated Aug. 1, 2006.

(Continued)

Primary Examiner — Lore Jarrett
(74) Attorney, Agent, or Firm — Kratz, Quintos & Hanson, LLP

(57) ABSTRACT

There is provided a dispensing mechanism for a liquid to be dispensed that does not damage microspherical bodies such as an erythrocyte and a liposome in the liquid to be dispensed when the liquid to be dispensed such as a sample and test liquid is sucked/discharged with a pipette.

When a liquid to be dispensed of a sample or a test liquid being an object to be measured includes a microspherical body, and the microspherical body is one with such property that it may be damaged when being contacted with a liquid having an osmotic pressure different from that of the liquid in the microspherical body, the damage of the microspherical body is prevented by sequentially sucking a gas, a solution exhibiting an osmotic pressure that does not damage the microspherical body in the liquid to be dispensed and not having a bad effect on the measurement, the gas, and the liquid to be dispensed in a pipette the inside of which is filled with a liquid, because the pipette inside wall is substituted with the solution having an osmotic pressure that does not damage the microspherical body.

9 Claims, 1 Drawing Sheet

OTHER PUBLICATIONS

Monroe, Dan, "Novel Liposome Immunoassays for Detecting Antigens, Antibodies, and Haptens," J. of Liposome Research, 1989-90, 1(3), pp. 339-377 (specification, p. 15).

Yamamoto, Sachiko, et al., "Automated Homogenous Liposome-Based Assay System for Total Complement Activity," Clin. Chem., 1995, 41/4, pp. 586-590 (specification p. 15).

* cited by examiner

DISPENSING MECHANISM, DISPENSING APPARATUS AND DISPENSING METHOD FOR LIQUID TO BE DISPENSED

TECHNICAL FIELD

The present invention relates to a dispensing mechanism, a dispensing apparatus and a dispensing method for a liquid to be dispensed such as samples and test liquids used for autoanalyzers. More particularly, it relates to a dispensing mechanism, a dispensing apparatus and a dispensing method for a liquid to be dispensed capable of sucking/discharging microspherical bodies, such as an erythrocyte and a liposome included in the liquid to be dispensed without the anxiety about burst thereof.

BACKGROUND ART

In autoanalyzers, a pipette (probe) for dispensing a sample is used for dispensing the sample from a sample tube to a cell.

For the pipette, the inside thereof is filled with a liquid (prime water) such as purified water for the purpose of collecting/dispensing a minute amount of sample with high accuracy. This is because, by sucking/discharging the sample via the liquid, the minute amount of sample can be sucked/discharged with high accuracy.

Conventionally, air and a sample are sequentially sucked into a pipette filled with prime water, and then the sample is discharged to a measuring cell.

DISCLOSURE OF THE INVENTION

Problems to be Solved by the Invention

However, for example, when a sample contains an erythrocyte, such as whole blood, there is a problem that the erythrocyte is occasionally damaged by the prime water to generate a hemolysis phenomenon, since prime water adheres to a pipette inner wall at the time of collecting the sample with the pipette. Accordingly, there is a problem that the phenomenon may interfere with the measurement (for example, measurement error is generated). This is because, when the hemolysis occurs, for example, materials contained inside the erythrocyte (such as GOT, LDH, acid phosphatase, alkaline phosphatase, cholesterol, iron and protein) and colored materials such as hemoglobin have a bad effect on the measurement.

Meanwhile, such an idea is tried that air is sucked before a sample being sucked so as to prevent the direct contact of the sample with the purified water, not to allow the sample and the purified water to contact with each other at the time of collecting the sample with the pipette. However, it was difficult to prevent the purified water remaining on the pipette wall surface, and, therefore, to prevent the occurrence of the hemolysis phenomenon in the case where the sample is whole blood.

In addition, there is occasionally a case that a washing liquid adheres to the pipette outer wall at the time of washing the pipette, and that the adhering washing liquid also has a bad effect on the sample. Solving the problem has been also desired.

The present invention has been accomplished while focusing attention on these points, and is intended to provide a dispensing mechanism, a dispensing apparatus and a dispensing method for a liquid to be dispensed that do not damage microspherical bodies such as, for example, an erythrocyte and a liposome in the liquid to be dispensed, when liquids to be dispensed such as a sample and a test liquid are sucked/discharged with a pipette.

Means for Solving the Problems

The dispensing mechanism of the present invention that suits the above purpose is characterized in that a liquid to be dispensed includes a microspherical body and the microspherical body is one with such property that it may be damaged when being contacted with a liquid having an osmotic pressure different from that of the liquid in the microspherical body, wherein the mechanism has such function as sequentially sucking a gas not having a bad effect on measurement, a solution exhibiting an osmotic pressure that does not damage the microspherical body in the liquid to be dispensed and not having a bad effect on the measurement, the gas, and the liquid to be dispensed in a pipette the inside of which is filled with a liquid, and discharging the sucked liquid to be dispensed into a vessel.

The mechanism, wherein the liquid filled in the inside of the pipette is prime water (purified water) and is provided with the function of washing the inside with the liquid after the discharge, is preferable (claim 2).

As the liquid to be dispensed, whole blood is preferable because of a high frequency of usage (claim 3). As the solution, physiological saline is preferable because of low price (claim 4).

The dispensing apparatus of the present invention is characterized in that a liquid to be dispensed includes a microspherical body, and the microspherical body is one with such property that it may be damaged when being contacted with a liquid having an osmotic pressure different from that of the liquid in the microspherical body, wherein the apparatus has such mechanism as sequentially sucking a gas not having a bad effect on measurement, a solution exhibiting an osmotic pressure that does not damage the microspherical body in the liquid to be dispensed and not having a bad effect on the measurement, the gas, and the liquid to be dispensed in a pipette the inside of which is filled with a liquid, and a mechanism of discharging the sucked liquid to be dispensed into a vessel (claim 5).

The dispensing method of the present invention is characterized in that a liquid to be dispensed includes a microspherical body, and the microspherical body is one with such property that it may be damaged when being contacted with a liquid having an osmotic pressure different from that of the liquid in the microspherical body, wherein the method comprises the steps of sequentially sucking a gas not having a bad effect on measurement, a solution exhibiting an osmotic pressure that does not damage the microspherical body in the liquid to be dispensed and not having a bad effect on the measurement, the gas, and the liquid to be dispensed in a pipette the inside of which is filled with a liquid, and discharging the sucked liquid to be dispensed into a vessel (claim 6).

The depth of dipping the pipette at the time of collecting the solution exhibiting the osmotic pressure that does not damage the microspherical body in the liquid to be dispensed and not having a bad effect on the measurement is preferably a depth more than or equal to that at the time of sucking the liquid to be dispensed, because the burst of the microspherical body can be prevented even when the washing water adheres to the pipette outer wall (claim 7).

Effect of the Invention

According to the present invention, upon sucking/discharging a liquid to be dispensed such as a sample or reagent with a pipette, since the pipette inner wall with which the liquid to be dispensed contacts is coated with a solution exhibiting an osmotic pressure that does not damage the microspherical body in the liquid to be dispensed and not having a bad effect on the measurement, microspherical bodies in the liquid to be dispensed such as an erythrocyte and a liposome are not damaged even when the liquid to be dispensed contacts with the inner wall, to give a significantly improved measurement accuracy.

BEST MODE FOR CARRYING OUT THE INVENTION

Figure 1:
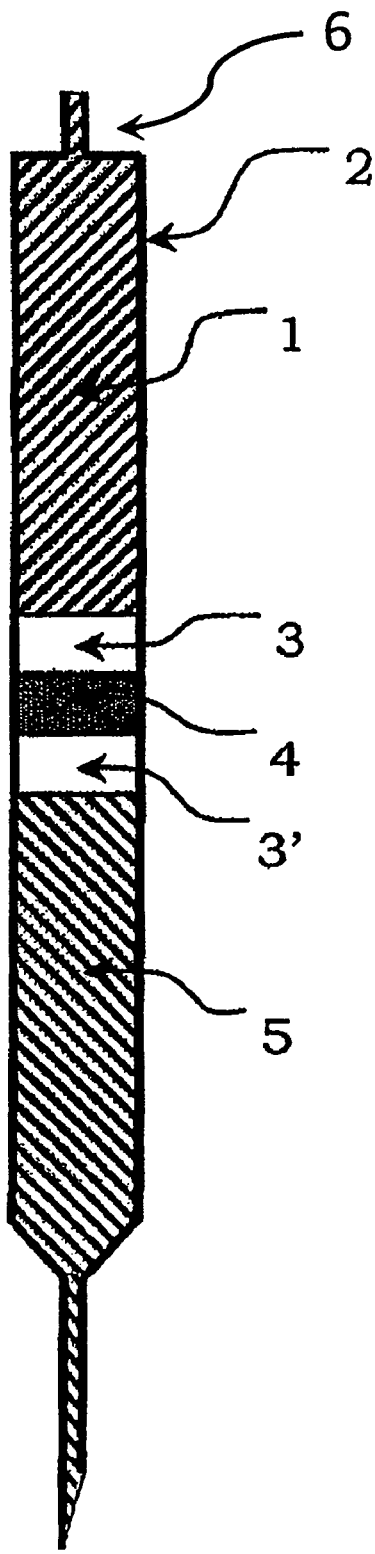
FIG. 1 is a rough side view showing one Example of the present invention.
1: prime water (purified water)
2: pipette (probe)
3,3': air (gas)
4: physiological saline
5: whole blood

Next, the embodiment of the present invention will be described based on the drawing.

FIG. 1 is a rough view showing one Example of the present invention, and shows a state in which air 3, physiological saline 4, air 3' and whole blood 5 being a liquid to be dispensed have sequentially been sucked in a pipette 2 (probe) filled with prime water 1. Meanwhile, the liquid to be dispensed is sucked/discharged by reducing or applying pressure from a thin tube 6 connected to the top of the pipette 2.

The physiological saline 4 does not directly contact with the prime water 1 or the whole blood 5 via the air 3 or 3', therefore it is possible to maintain the salt concentration thereof at an approximately constant level from the initiation of the suction to the achievement of the state in FIG. 1. The concentration has been set to a concentration that does not damage the erythrocyte in the whole blood being the liquid to be dispensed. Further, by sucking the physiological saline into the pipette, the pipette inner wall and the prime water adhering/remaining thereon are displaced and coated with the saline solution having concentration that does not damage the erythrocyte. As the result, when the erythrocyte contacts with it, there is no anxiety about the burst of a part of the erythrocyte.

That is, upon sucking a liquid to be dispensed, conventionally prime water (purified water) adheres/remains on the pipette inner wall, and, by the contact of the sucked liquid to be dispensed with the remaining prime water (purified water), microspherical bodies in the liquid to be dispensed are occasionally damaged. In contrast, in the present invention, since the solution exhibiting an osmotic pressure that does not damage the microspherical bodies and not having a bad effect on the measurement is sucked prior to the suction of the liquid to be dispensed, the prime water (purified water) being adsorbed and remaining on the pipette inner wall is substituted by the solution (solution exhibiting an osmotic pressure that does not damage microspherical bodies), to make it possible to avoid the damage of microspherical bodies (such as the hemolysis phenomenon) due to the contact of the prime water (purified water) with the liquid to be dispensed (whole blood).

A part of microspherical bodies in a liquid to be dispensed occasionally burst due to a washing liquid adhering to the pipette outer wall. In order to surely prevent this further, it is preferable to set the depth of pipette immersion upon collecting the physiological saline to the depth more than or equal to that upon collecting the liquid to be dispensed.

From the state in FIG. 1, the liquid to be dispensed (whole blood) is discharged in a separating cell (vessel). Upon the suction/discharge, no prime water (purified water) adheres/remains on the pipette inner wall, which is coated with physiological saline. Therefore, the conventional hemolysis phenomenon due to the contact of the prime water (purified water) adhering/remaining on the pipette inner wall with a liquid to be dispensed (whole blood) can be avoided. In this Example, there is specifically shown only processes up to the step of sucking whole blood being the liquid to be dispensed by the method of the present invention. But, subsequently, measurement can be performed, for example, according to the following operations.

That is, the whole blood 5 having been sucked as described above is dispensed into a separation cell, which is then subjected to centrifugation to give plasma. The plasma is moved to a reaction cell, to which a reagent is added to react. Thus, the component in the plasma can be measured.

The above-described "solution exhibiting an osmotic pressure that does not damage microspherical bodies in a liquid to be dispensed and not having a bad effect on the measurement" is a solution exhibiting such osmotic pressure as described above, in other words, normally a solution exhibiting an osmotic pressure higher than the osmotic pressure that bursts microspherical bodies, preferably a solution exhibiting the same degree of osmotic pressure as that of the liquid in the microspherical body (isotonic liquid or nearly isotonic liquid) and not containing a component that have a bad effect on the measurement.

Although in the above Example, physiological saline was used, other solutions may be used only when they exhibit osmotic pressures that do not damage microspherical bodies in a liquid to be dispensed, and they do not have a bad effect on the measurement.

The osmotic pressure that does not damage microspherical bodies in a sample means an osmotic pressure higher than the one that bursts (damages) the microspherical body in a liquid to be dispensed, and is preferably an osmotic pressure approximately the same as that of the liquid in the microspherical body (osmotic pressure of an isotonic liquid or nearly isotonic liquid).

Such osmotic pressure can not be categorically defined, because it depends on kinds of microspherical bodies, kinds of liquids in microspherical bodies, and the like. But, more specifically, for example, when the microspherical body is an erythrocyte, the lower limit of osmotic pressure is usually higher than 170 mOsm/L, preferably 200 mOsm/L or more, more preferably 239 mOsm/L or more, further preferably 250 mOsm/L or more, particularly preferably 290 mOsm/L, and the upper limit of osmotic pressure is usually 1026 mOsm/L or less, preferably 800 mOsm/L or less, more preferably 500 mOsm/L or less, further preferably 341 mOsm/L or less, particularly preferably 324 mOsm/L or less. Above all, around 300 mOsm/L is particularly preferable. In addition, for example, when the microspherical body is a liposome, the osmotic pressure may suitably be selected in accordance with kinds of components constituting the membrane, osmotic pressures shown by the encapsulated solution and the like. For example, when the encapsulated solution is a solution that exhibits approximately the same osmotic pressure as that of physiological saline, the equivalent range for the above-described case of erythrocyte is preferable.

As such solution, solutions having ionic strengths that exhibit osmotic pressures as described above and not having a bad effect on the measurement are sufficient.

Specifically, there are included aqueous solutions having a prescribed concentration of, for example, halides (such as F, Cl, Br and I) of alkali metals (such as Na, K and Li), Mg, Ca, ammonium and the like, and aqueous solutions having a prescribed concentration of, for example, salts (for example, salts of alkali metals such as Na, K and Li, ammonium salts and the like) of sulfuric acid, phosphoric acid, carboxylic acids (oxalic acid, acetic acid, succinic acid, lactic acid, tartaric acid, citric acid and the like), which do not have a bad effect on the measurement.

Here, "do not have a bad effect on the measurement" has the meaning similar to "do not contain a component having a bad effect on the measurement," and intended solution that does not have a bad effect on the measurement may suitably be selected from solutions as described above, while taking the measurement object, measurement principle and the like into consideration.

For example, ammonium, Mg and the like occasionally affect measuring urea nitrogen value in a sample, and, therefore, are suitably used for measuring objects other than urea nitrogen value. In addition, lactates and oxalates occasionally affect measuring LDH, GPT and the like; Mg, Ca and the like occasionally affect measuring Mg and Ca; and phosphates occasionally affect measuring inorganic phosphorus. Therefore, these reagents may desirably be used for measuring intended objects other than these.

Further, Ca salts and Mg salts occasionally generate a precipitate depending on the concentration used, and attention should be paid.

Among above-described solutions, an aqueous NaCl solution, an aqueous KCl solution, an aqueous sodium sulfate solution, an aqueous potassium sulfate solution and the like are preferable, and an aqueous NaCl solution (physiological saline) is particularly preferable because it is inexpensive.

The concentration of the above-described aqueous solutions may be set so as to show the above-described osmotic pressure and is not particularly limited. The concentration can not be categorically defined because it depends on kinds of solutions to be used, kinds of microspherical bodies, kinds of liquids in microspherical bodies and the like, but, more specifically, when an aqueous NaCl solution (physiological saline) is used as the solution and the microspherical body is an erythrocyte, the lower limit of the NaCl concentration is usually higher than 0.5% (w/v), preferably 0.59% (w/v) or more, more preferably 0.7% (w/v) or more, further preferably 0.73% (w/v) or more, particularly preferably 0.85% (w/v), and the upper limit of the NaCl concentration is usually 3% (w/v) or less, preferably 2.35% (w/v) or less, more preferably 1.47% (w/v) or less, further preferably 1% (w/v) or less, particularly preferably 0.95% (w/v) or less. Above all, near 0.88% (w/v) is particularly preferable. Further, for example, when the microspherical body is a liposome, the NaCl concentration may suitably be selected in accordance with kinds of components constituting the membrane, osmotic pressures exhibited by the encapsulated solution, and the like. For example, when the encapsulated solution is one that exhibits the same degree of osmotic pressure as that of physiological saline, the concentration is preferably within the same range as that of the above-described case of erythrocyte.

In the above Example, whole blood was used as the liquid to be dispensed, but other liquids to be dispensed may also be applied to the invention of the present application, only when they are solutions each containing a microspherical body having property that it may be damaged when being contacted with a liquid having an osmotic pressure different from that of the liquid in the microspherical body.

As such microspherical bodies, microspherical bodies formed of a semipermeable membrane are included. For example, there are included microspherical bodies in a living body (formed of a biological membrane) such as an erythrocyte, a leukocyte and a thrombocyte, and microspherical bodies formed of a synthesized membrane, such as a liposome.

For the solution including microspherical bodies (liquid to be dispensed), a solution including the above-mentioned microspherical body is sufficient. For example, there are mentioned body fluids including a microspherical body such as whole blood, solutions obtained by diluting or suspending the above-described microspherical bodies with, for example, water, physiological saline, buffer solutions usually used in the field (such as PBS buffer, phosphate buffer, borate buffer, Tris buffer, phosphate buffer, veronal buffer, borate buffer and Good's buffer), and the like. "The property that it may be damaged when being contacted with a liquid having an osmotic pressure different from that of the liquid in the microspherical body" means that, when a microspherical body is contacted with a liquids having an osmotic pressure different from that possessed by the liquid in the microspherical body, the membrane structures forming the microspherical body is damaged due to the difference in osmotic pressures, and that the component in the microspherical body flow out to the outside of the microspherical body. Generally, it means such property that, when a microspherical body is contacted with a liquid having a lower osmotic pressure (hypotonic fluid) than the osmotic presser possessed by the liquid in the microspherical body, the microspherical body expands due to the transfer of water from the liquid having a lower osmotic pressure (hypotonic fluid) into the microspherical body to burst (be damaged) finally.

Meanwhile, for the liposome, all of them that are usually used in the field are usable, and, for example, there are included ones that are prepared by publicly known preparation methods [such as J. Liposome Res., 1(3), 339-377 (1989-90); Clin. Chem. 41/4. 586-590 (1995)], while using natural lecithin such as egg yolk lecithin, phospholipid such as distealoyl phosphatidylcholine, dimyristoyl phosphatidyl glycerol (DMPG) and egg yolk phosphatidyl glycerol, glycolipid such as ganglioside glycolipid, mixtures of these and cholesterols, or combinations of these and lipopolysaccharide or the like as a starting material. In addition, in the liposome, for example, enzyme, coenzyme, a substrate for enzyme, dye, a fluorescent material, a light-emitting material, sugars, an ionic compound, a chelating indicator, dye and a spin label compound may be encapsulated by publicly known preparation methods (such as Japanese Unexamined Patent Publications No. 7-110331 and No. 7-140147).

In the above-described Example, physiological saline was sucked so as to stay between airs. But, other gases except air are acceptable only when they do not have a bad effect on the measurement. For example, when the pipette is placed in a nitrogen atmosphere, the nitrogen can be used. Also, in the same way, an inert gas such as argon or helium is usable.

In the present invention, in order to collect/dispense a minute amount of liquid to be dispensed with high accuracy, the inside of the pipette is filled with a liquid (prime water) such as distilled water, purified water, or an inert and insulating oil such as silicone oil.

In the above Example, a pipette provided with a liquid level sensor, which detects a liquid level by catching the variation of capacitance, was used. Therefore, the liquid 1 must be a liquid containing no electrolyte. This is because, if the liquid 1 contains an electrolyte, the liquid level detection based on capacitance becomes impossible.

The invention claimed is:

1. A method for dispensing a liquid to be dispensed that includes a microspherical body, wherein the microspherical body is one with such property that it may be damaged when being contacted with a liquid having an osmotic pressure different from that of the liquid in the microspherical body, comprising the steps of sequentially sucking a gas not having a bad effect on measurement for forming a first gas layer, a solution exhibiting an osmotic pressure that does not damage the microspherical body in the liquid to be dispensed and not having a bad effect on the measurement, the gas again for forming a second gas layer, and the liquid to be dispensed into a pipette that is filled with a prime liquid, and discharging the sucked liquid to be dispensed into a vessel, wherein the solution differs in content from the liquid to be dispensed.

2. The method for dispensing a liquid to be dispensed according to claim 1, wherein the depth of dipping the pipette at the time of collecting the solution exhibiting the osmotic pressure that does not damage the microspherical body in the liquid to be dispensed and not having a bad effect on the measurement is a depth more than or equal to that at the time of sucking the liquid to be dispensed.

3. The method according to claim 2, wherein the solution is physiological saline.

4. The method according to claim 1, wherein the liquid to be dispensed is whole blood.

5. The method according to claim 4, wherein the solution is physiological saline.

6. The method according to claim 1, wherein the solution is physiological saline.

7. The method according to claim 1, wherein the microspherical body is an erythrocyte and the solution has an osmotic pressure in a range of 170 mOsm/L to 800 mOsm/L.

8. The method according to claim 1, wherein the solution does not include lactate and does not include oxalate.

9. The method according to claim 1, wherein the solution does not include Mg and does not include Ca.

* * * * *